United States Patent [19]

de Klein

[11] 4,014,910

[45] Mar. 29, 1977

[54] PROCESS FOR THE PREPARATION OF AN (AR)ALKANE CARBOXYLIC ACID

[75] Inventor: Willem J. de Klein, Dieren, Netherlands

[73] Assignee: Akzo N.V., Arnhem, Netherlands

[22] Filed: Sept. 15, 1975

[21] Appl. No.: 613,322

Related U.S. Application Data

[63] Continuation of Ser. No. 382,165, July 24, 1973, abandoned.

[30] Foreign Application Priority Data

Aug. 1, 1972 Netherlands .................. 7210545

[52] U.S. Cl. .................. 260/413; 260/343.6; 260/346.1 R; 260/515 R; 260/533 R; 260/533 N; 260/546

[51] Int. Cl.² ............... C07C 51/00; C07C 53/22; C07C 63/00

[58] Field of Search .......... 252/413, 515 R, 533 R, 252/533 N

[56] References Cited

UNITED STATES PATENTS

| | | | |
|---|---|---|---|
| 2,297,039 | 9/1942 | Van Melson | 260/537 |
| 2,479,082 | 8/1949 | Roland et al. | 260/413 |
| 2,496,358 | 2/1950 | Ramsay et al. | 260/413 |
| 3,054,814 | 9/1962 | Jason et al. | 260/413 |
| 3,720,710 | 4/1973 | Norton et al. | 260/533 |

FOREIGN PATENTS OR APPLICATIONS 734,184  6/1969  Belgium .................. 260/413

*Primary Examiner*—Patrick P. Garvin
*Assistant Examiner*—P. E. Konopka
*Attorney, Agent, or Firm*—Stevens, Davis, Miller & Mosher

[57] ABSTRACT

A process is disclosed for making an (ar)alkane carboxylic acid in high yield when reacting an (ar)alkene with a carbonyl compound having at least one hydrogen atom attached to the alpha-carbon atom in the presence of a manganese compound which is at least trivalent by observing the following reaction parameters: (a) having at least 60% by weight of a carboxylic anhydride in the carbonyl compound, (b) having a manganese compound concentration of from $10^{-3}$ to $10^{-10}$ moles/l and (c) maintaining the (ar)alkene concentration below 0.1 mole/l.

12 Claims, No Drawings

PROCESS FOR THE PREPARATION OF AN (AR)ALKANE CARBOXYLIC ACID

This is a continuation of application Ser. No. 382,165, filed July 24, 1973, now abandoned.

The present invention relates to a process for the preparation of an (ar)alkane carboxylic acid carried out by reacting an (ar) alkene in the presence of a manganese compound, which is at least trivalent, with a carbonyl compound having at least one hydrogen atom attached to the alpha-carbon atom.

In the specification and claims, the term (ar)alkane carboxylic acid refers to an aliphatic or an araliphatic carboxylic acid and an (ar)alkene means an olefin provided that if the olefin contains an aromatic ring there will be at least one carbon atom between the ethylene group and the aryl group.

A process similar to the instant case is described in the Belgian Patent Specification 734,184 and while this known process may give a good yield of (ar)alkane carboxyline acid, this acid, upon further analysis is found largely to consist of a reaction product in which two carbonyl compounds are bonded to said (ar)alkene per ethylene group of the (ar)alkene one of which compounds can be removed by hydrolysis. If the carbonyl compound is a combination of acetic acid and acetic anhydride, the product formed will mainly be gamma-acetoxyalkanoic acid in the case of an alpha-olefin instead of the commercially far more important alkanoic acid without an acetoxy group in the gamma position. In Example I of the afore-mentioned patent specification, using as starting materials octene-1 and a mixture of 500 ml of acetic acid and 100 ml of acetic anhydride with manganese dioxide as a coupling reagent, there is obtained a 75% yield of n-decanoic acid. However, the percentage indicated can only have been arrived at due to a misinterpretation of the results of the analysis. The same comment applies with respect to Example IX of the Belgian patent specification.

The present invention provides a process by which the above-described drawback (the bonding of two carbonyl compounds to the (ar)alkene) is largely obviated.

Concentrations expressed in moles per liter (moles/l) indicates hereinafter the number of gram-molecules per liter.

The invention is characterized in that in a process of the afore-mentioned known type:
a. the carbonyl compound contains at least 60% by weight of a carboxylic anhydride;
b. the trivalent manganese compound is present in an amount in the range of $10^{-3}$ to $10^{-10}$ moles/1; and
c. the (ar)alkene concentration is lower than 0.1 mole/1.

In this way it is possible to prepare an (ar)alkane carboxylic acid with only one carboxyl group per ethylene group in a yield of at least 70%.

If one calculates the acid yield on the trivalent manganese added, the acid yield may be greater than 400%. An important additional advantage of the process according to the invention is that more than 95% of the bivalent manganese compound which forms during the reaction process can readily be removed by simple filtration techniques.

The invention is based on the knowledge that the reaction proceeds in accordance with a radical mechanism which can be formulated as follows, HoAc and Ac$_2$O representing, acetic acid and acetic anhydride, respectively. The initiation proceeds thusly:

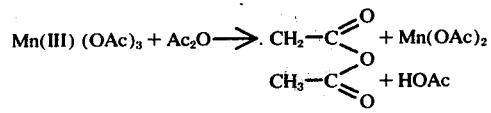

It has been found that

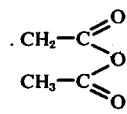

can readily be bonded to an ethylene group, as shown in the following equation:

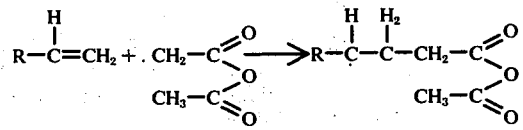

The addition product again is a radical, so that it will show a tendency to react rapidly with another molecule.

Since the reaction mixture is formed by dissimilar components different types of reactions may occur. It will be clear that the higher the proportion of a given component, the greater the chance of the radical reacting therewith. In the presence of a relatively high proportion of acetic anhydride the mixed anhydride of the desired alkanoic acid will form, and a new radical

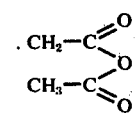

will result:

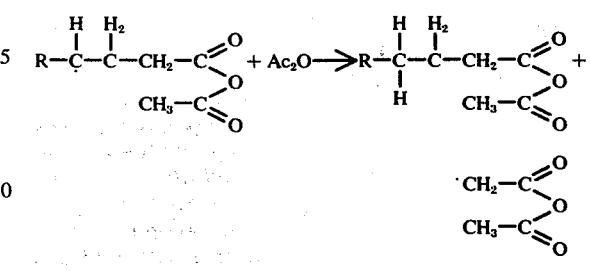

It is therefore evident that the presence of a high carbonic anhydride concentration is of great importance.

The use of trivalent manganese will cause the reaction to proceed as follows:

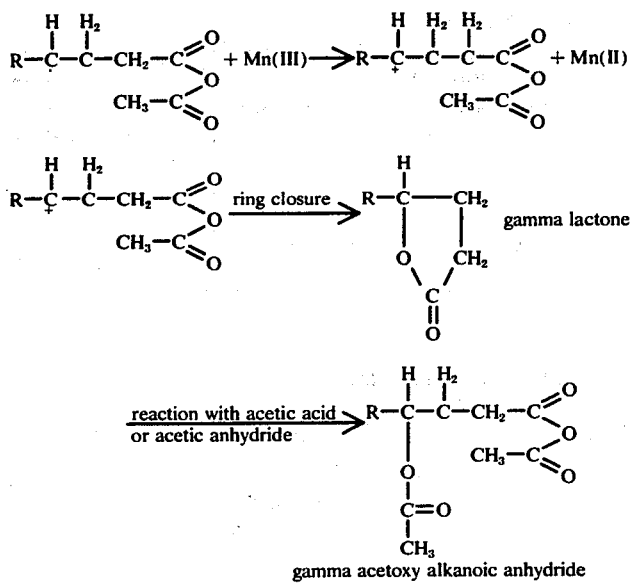

gamma lactone gamma acetoxy alkanoic anhydride

It is recommended that the trivalent manganese concentration should be kept low to counteract the undesirable side reaction as much as possible.

On the assumption of the reaction mechanism operating according to the invention, another important side reaction may take place, viz. telomerization, involving reaction of the radical with an alkene (for instance, an alphaolefin) to form a dimer:

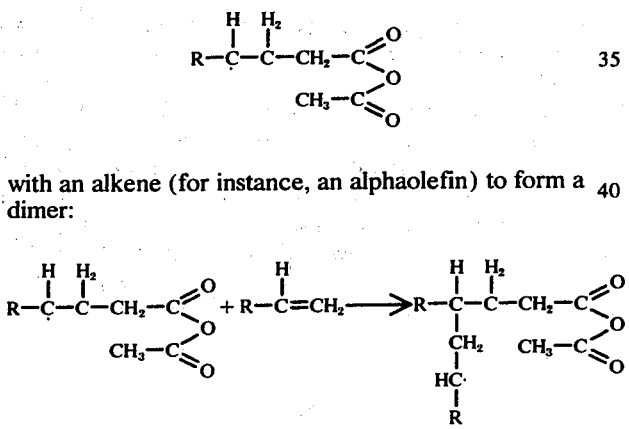

This dimer radical may in its turn react with $Ac_2O$ to form a dimer-branched acid; alternatively, it may react with trivalent manganese, etc.

Here it appears to be of great importance for the (ar)alkene concentration to be not unduly high.

The presence of the carbonyl compound in the form of carboyxlic anhydride in an amount of less than 60% by weight will give rise to the formation of a relatively large amount of by-products as a result of dimerization, the formation of lactone, etc. therefore causing the process proposed to be less attractive economically.

This applies to the use of a concentration of a trivalent manganese compound greater than $10^{-3}$ moles/l, whereas at a concentration lower than $10^{-10}$ moles1 the reaction speed will be so low that the process is no longer attractive from a commercial point of view.

For the alkene concentration it also holds that it must not be higher than 0.1 mole/l, in order to prevent the formation of an unduly large amount of by-products, which in this case would consist of dimers and telomers for the greater part.

The most favorable results are found to be obtained if the process according to the invention is carried out with the concentration of the trivalent manganese compound in the range of $10^{-5}$ to $10^{-7}$ moles/l, preferably approximately $10^{-6}$ moles/l.

The (ar)alkene concentration is somewhat less critical than the concentration of the trivalent manganese compound, but for optimum results it should be in the range of $10^{-4}$ to $10^{+5}$ moles/l.

The (ar)alkenes suitable for carrying out the process according to the invention include cyclic and acyclic olefins. They may be substituted or non-substituted and contain several unsaturated ethylene groups. It is important that the carboxylic anhydrides used dissolve at temperatures in the range of approximately 50° to 250° C, in which range the reaction speed is reasonably high. Examples of such (ar)alkenes are all types of alpha-olefins, having from 2 to 22 carbon atoms exemplified by 1,3-butadiene, 1,5-hexadiene, allylbenzene, cyclooctene, cyclo-hexene, etc.

The carbonyl compounds to be used for carrying out the process according to the invention include the anhydrides of the following acids: acetic acid, propionic acid, octanoic acid, phenylpropionic acid, stearic acid, etc. The acids may, of course, carry substituents, provided that the carbon atom, which is in the alpha-position relative to the carbonyl radical, contains at least one hydrogen atom.

For practical reasons it is preferred to use the anhydrides of lower fatty acids such as acetic acid and isobutyric acid, as they can readily be isolated from the reaction mixture by distillation.

In general it is desired that the product to be obtained should be as homogeneous as possible. It is therefore preferred to use the trivalent manganese compound in the form of the salt of carboxylic acid, which is derived from the same carboxylic acid as used for building up the carboxylic anhydride. In this way the formation of various acid anhydrides is counteracted as far as possible.

The process according to the invention may be carried out in one of several ways. In order to prevent the subsequent working up of the reaction mixture from becoming too expensive owing to the presence of large amounts of solvent as a result of the highly diluted concentration of the components taking part in the reaction, it is preferred that the trivalent manganese should be gradually added to the reaction mixture. During the addition the carboxylic acid formed separates as an anhydride without large amounts of undesired by-products being formed as a result of side reactions.

Despite the low concentration of one of the reaction components it is possible to obtain a high degree of conversion per unit volume of the reactor, provided that the reaction mixture is properly mixed. A proper mixing is also of great importance to avoid the occurrence of locally too high concentrations, which may give rise to the afore-mentioned side reactions.

As stated above, the (ar)alkene concentration is less critical than the trivalent manganese concentration; but here also the most favorable results are obtained if the (ar)alkene is added gradually to the reaction mixture.

The temperature at which the process according to the invention may successfully be carried out varies from approximately 50° C to approximately 250° C, depending on the reaction components used. It is preferred that the temperature range between 70° and 200° C.

If the acetic anhydride contains relatively large proportions of acetic acid and water or if instead of anhydrous Mn(OAc)₃ use is made of Mn(OAc)₃ 2 aq., it is preferred that the reaction temperature be above the boiling point of water and above that of the carboxylic acid derived from the anhydride used but below the boiling point of the carboxylic anhydride used.

It will be clear that the reaction also may be carried in a autoclave at elevated pressure. In view of the boiling points of the reaction components it may be desirable that the reaction be carried out at reduced pressure in some cases.

The reaction may be carried out batch-wise or in a continuous process. In the latter case, it may be advantageous if the (ar)alkene, the trivalent manganese compound and the carboxylic anhydride are slowly added to the reaction mixture in the reactor, with proper mixing, after which at the top of the reactor the water and carboxylic acid which may have formed are carried off while in the vapor phase, followed by having the carboxylic anhydride containing the reaction product, discharged via the bottom of the reactor, cooled, filtered and isolated. The carboyxlic anhydride evolved in the purification may again be added to the reaction mixture.

The invention will be described further in the following examples. The examples, of course, merely serve to elucidate the invention and are not to be considered a limitation upon the scope thereof.

EXAMPLE I (Comparative Example in conformity with the Belgian Patent Specification 734,184)

Following Example IX of Belgian Patent Specification 734,184, 0.318 moles of n-octene (50 ml) and 0.1 mole (23.2 g) of Mn(OAc)₃ were mixed with 600 ml of cetic acid and 100 ml of acetic anhydride in nitrogen atmosphere. The mixture was heated to 110° C until the color of the trivalent manganese had disappeared.

Upon cooling of the mixture no bivalent manganese compound separated out. After evaporation of the acetic acid/acetic anhydride mixture, water was added to the residue, which was subsequently kept for 48 hours. Acidification with sulfuric acid was followed by ether extraction. The ether extract was isolated and subsequently evaporated. The resulting residue weighed 10.65 g and contained 5.5% by weight of decanoic acid implying that the yield of decanoic acid is as low as 3.4%, calculated on the amount of trivalent manganese added. Gas chromatographic analysis revealed the presence of a large number of by-products.

EXAMPLE II

In an atmosphere of nitrogen a slurry of 0.025 moles Mn(OAc)₃ in 200 ml acetic anhydride was, with proper stirring, slowly added to 300 ml of acetic anhydride maintained at a temperature of 122° C. Simultaneously 0.2 moles (22.4 g) of n-octene were slowly added to the acetic anhydride in small amounts. The rate at which the Mn(OAc)₃ was added to the reaction mixture was such as to permit the mixture to retain a pale pink color. The reaction mixture was then cooled down to room temperature, the Mn (OAc)₂ precipitating almost quantitatively (97.5% by weight), and filtered off. The acetic anhydride was removed from the filtrate by distillation. An infrared spectrum of the residue revealed a strong absorption of anhydride groups. It was heated under reflux with acetic acid with a drop of a mineral acid being added to the mixture.

After 2 ½hours the mixture of acetic acid and acetic anhydride was removed by distillation. The weight of the residue was 28.2 g. An infrared spectrum showed strong absorption bands of a carboxyl group.

Gas chromatographic analysis revealed that the residue contained decanoic acid in an amount of 58.7% by weight. This corresponds to a yield of 386%, calculated on the Mn(OAc)₃ added.

Gel-Permeation-Chromatography analysis pointed to the presence of telomers, which were identified by means of mass spectroscopy, Nuclear-Magnetic-Resonance and infrared spectroscopy. The dimer was a gamma-branched $C_{18}$ acid.

EXAMPLE III

The experiment described in Example II was repeated using n-dodecene in place of n-octene. After completion of the reaction acetic anhydride was distilled off, followed by heating the residue under reflux with acetic acid.

Evaporation of the acetic acid/acetic anhydride mixture resulting in 36.1 g of solid white product, which contained 72% by weight of myristic acid. This is equivalent to a yield of 456%, calculated on the Mn(OAc)₃ added.

EXAMPLE IV

Example II was repeated using trivalent manganese isobutyrate in place of trivalent manganese acetate and isobutyric acid anhydride instead of acetic anhydride.

The reaction was carried out at a temperature of 140° C.

After evaporation of the isobutyric acid, the residue was added to 450 ml of water. After about 12 hours the mixture was acidified with sulfuric acid and extracted with diethylether. After evaporation of the ether, the resulting residue was found to contain substantially alpha, alpha'dimethyldecanoic acid.

What is claimed is:

1. In a process for the preparation of a carboxylic acid through hydrolysis of the product, obtained by reaction under inert conditions and in the presence of a trivalent manganese compound, of an ethylenically unsaturated hydrocarbon compound with a carbonyl compound having at least one hydrogen atom attached to an alpha-carbon atom, the improvements comprising:
   a. using for the carbonyl compound a member selected from the group consisting of a lower carboxylic anhydride and a mixture of a lower carboxylic anhydride and a lower carboxylic acid wherein the acid is present in an amount up to 40% by weight,
   b. employing the trivalent manganese compound in an amount of $10^{-3}$ to $10^{-10}$ moles/liter, and
   c. maintaining the concentration of the ethylenically unsaturated hydrocarbon below 0.1 mole/liter.

2. The process of claim 1 wherein said carbonyl compound contains at least 95% by weight of the carboxylic anhydride.

3. The process of claim 1 wherein the manganese compound is present in an amount of $10^{-5}$ to $10^{-7}$ mole/l.

4. The process of claim 1 wherein the concentration of said ethylenically unsaturated hydrocarbon compound is $10^{-4}$ to $10^{-5}$ moles/l.

5. The process of claim 1 wherein said manganese compound is employed as a salt of a carboxylic acid related to said carboxylic anhydride.

6. The process of claim 1 wherein said manganese compound is gradually added to the reaction mixture.

7. The process of claim 1 wherein said ethylenically unsaturated hydrocarbon compound is gradually added to the reaction mixture.

8. The process of claim 1 wherein the reaction is carried out at a temperature above the boiling point of water and above that of the carboxylic acid derived from the anhydride used but below the boiling point of the carboxylic anhydride used.

9. The process of claim 1 wherein the process is carried out continuously in a reactor in such a way that the ethylenically unsaturated hydrocarbon compound, the manganese compound and the carboxylic anhydride are each separately and gradually added to the properly homogenized reaction mixture obtained, which mixture is heated at such a temperature that the resulting water and lower carboxylic acid can be discharged from the top of the reactor, whereas the heavier boiling products are continuously collected at the bottom of the reactor to be successively cooled, filtered and isolated.

10. The process of claim 1 wherein the anhydride is acetic anhydride.

11. A process for making a carboxylic acid which comprises
    reacting an alpha-olefin having from 2 to 22 carbon atoms
    with an anhydride of a lower fatty acid
    in a reaction mixture containing from $10^{-3}$ to $10^{-10}$ moles per liter of trivalent manganese compound
    and containing said alpha-olefin in a concentration below 0.1 mole per liter.

12. The process of claim 11 wherein said anhydride is mixed with a lower fatty acid and the mixture contains at least 60% by weight of the anhydride.

* * * * *

UNITED STATES PATENT AND TRADEMARK OFFICE
CERTIFICATE OF CORRECTION

PATENT NO. : 4,014,910
DATED : March 29, 1977
INVENTOR(S) : Willem J. De Klein

It is certified that error appears in the above-identified patent and that said Letters Patent are hereby corrected as shown below:

Item [73] Assignee: Akzo N.V., Arnhem, Netherlands should be changed to read -- [73] Assignee: Akzona Incorporated, Asheville, North Carolina -- .

Signed and Sealed this

Twenty-eighth Day of June 1977

[SEAL]

Attest:

RUTH C. MASON
*Attesting Officer*

C. MARSHALL DANN
*Commissioner of Patents and Trademarks*